United States Patent
Aronow et al.

(10) Patent No.: US 9,757,183 B2
(45) Date of Patent: Sep. 12, 2017

(54) MULTIPLE PARAMETER FAULT DETECTION IN ELECTROSURGICAL INSTRUMENT SHIELDS

(71) Applicant: Encision Inc., Boulder, CO (US)

(72) Inventors: Kurt Albert Aronow, Louisville, CO (US); David Newton, Longmont, CO (US); Don R. Boyle, Longmont, CO (US)

(73) Assignee: Encision Inc., Boulder, CO (US)

( * ) Notice: Subject to any disclaimer, the term of this patent is extended or adjusted under 35 U.S.C. 154(b) by 0 days.

(21) Appl. No.: 14/982,372

(22) Filed: Dec. 29, 2015

(65) Prior Publication Data

US 2016/0106494 A1 Apr. 21, 2016

Related U.S. Application Data

(60) Continuation of application No. 13/786,670, filed on Mar. 6, 2013, now Pat. No. 9,254,165, which is a division of application No. 12/257,562, filed on Oct. 24, 2008, now Pat. No. 8,460,284.

(60) Provisional application No. 60/982,990, filed on Oct. 26, 2007.

(51) Int. Cl.
```
A61B 18/14    (2006.01)
A61B 18/12    (2006.01)
A61B 18/16    (2006.01)
A61B 18/00    (2006.01)
```

(52) U.S. Cl.
CPC ...... *A61B 18/1233* (2013.01); *A61B 18/1206* (2013.01); *A61B 18/16* (2013.01); *A61B 2018/00648* (2013.01); *A61B 2018/00672* (2013.01); *A61B 2018/00702* (2013.01); *A61B 2018/00708* (2013.01); *A61B 2018/00779* (2013.01); *A61B 2018/00827* (2013.01);
(Continued)

(58) Field of Classification Search
CPC . A61B 18/16; A61B 18/1206; A61B 18/1233; A61B 2018/00708; A61B 2018/00875; A61B 2018/00827; A61B 2018/00892
USPC .......................... 606/32, 34, 35, 38
See application file for complete search history.

(56) References Cited

U.S. PATENT DOCUMENTS

| | | |
|---|---|---|
| 984,756 A | 2/1911 | Frisch |
| 1,754,806 A | 4/1930 | Stevenson |
| 2,004,559 A | 6/1935 | Wappler et al. |

(Continued)

FOREIGN PATENT DOCUMENTS

DE 3013784 10/1980

OTHER PUBLICATIONS

Landry II, Gerald Ernest, "US Office Action re U.S. Appl. No. 13/786,670", filed Jul. 17, 2015, p. 27, Published in: US.

(Continued)

*Primary Examiner* — Gerald Landry, II
(74) *Attorney, Agent, or Firm* — Neugeboren O'Dowd PC (57) ABSTRACT

A system and method for detecting faults within an electrosurgical instrument having a shield and an active electrode uses multiple possible fault conditions. In one embodiment the monitoring system comprises an electrosurgical generator coupled to the electrosurgical instrument and adapted to deliver power to the active electrode of the electrosurgical instrument, monitoring circuitry coupled to the electrosurgical generator and the electrosurgical instrument.

22 Claims, 6 Drawing Sheets

(52) U.S. Cl.
CPC ............... *A61B 2018/00875* (2013.01); *A61B 2018/00892* (2013.01)

(56) References Cited

U.S. PATENT DOCUMENTS

| | | | |
|---|---|---|---|
| 2,008,361 | A | 7/1935 | Rhinevault |
| 2,448,741 | A | 9/1948 | Scott et al. |
| 2,741,248 | A | 4/1956 | Woodhall |
| 3,070,132 | A | 12/1962 | Sheridan |
| 3,580,983 | A | 5/1971 | Jackson |
| 3,585,985 | A | 6/1971 | Gould |
| 3,601,126 | A | 8/1971 | Estes |
| 3,706,008 | A | 12/1972 | Kremer |
| 3,707,149 | A | 12/1972 | Hao et al. |
| 3,804,096 | A | 4/1974 | Gonser |
| 3,834,392 | A | 9/1974 | Lampman et al. |
| 3,838,242 | A | 9/1974 | Goucher |
| 3,895,635 | A | 7/1975 | Justus et al. |
| 3,898,991 | A | 8/1975 | Ikuno et al. |
| 3,905,373 | A | 9/1975 | Gonser |
| 3,913,583 | A | 10/1975 | Bross |
| 3,933,157 | A | 1/1976 | Bjurwill et al. |
| 3,946,738 | A | 3/1976 | Newton et al. |
| 3,963,856 | A | 6/1976 | Carlson et al. |
| 3,994,287 | A | 11/1976 | Turp et al. |
| 4,003,380 | A | 1/1977 | Wein |
| 4,084,594 | A | 4/1978 | Mosior |
| 4,181,131 | A | 1/1980 | Ogiu |
| 4,184,492 | A | 1/1980 | Meinke et al. |
| 4,200,104 | A | 4/1980 | Harris |
| 4,231,372 | A | 11/1980 | Newton |
| 4,237,887 | A | 12/1980 | Gonser |
| 4,248,716 | A | 2/1981 | LaValley |
| 4,303,073 | A | 12/1981 | Archibald |
| 4,311,144 | A | 1/1982 | Harada |
| 4,325,374 | A | 4/1982 | Komiya |
| 4,343,308 | A | 8/1982 | Gross |
| 4,367,746 | A | 1/1983 | Derechinsky |
| 4,374,517 | A | 2/1983 | Hagiwara |
| 4,410,925 | A * | 10/1983 | Tucker .................... H02H 3/17 361/42 |
| 4,449,532 | A | 5/1984 | Storz |
| 4,494,541 | A | 1/1985 | Archibald |
| 4,615,330 | A | 10/1986 | Nagasaki et al. |
| 4,617,927 | A | 10/1986 | Manes |
| 4,618,885 | A | 10/1986 | Nagasaki et al. |
| 4,638,802 | A | 1/1987 | Okada |
| 4,662,369 | A | 5/1987 | Ensslin |
| 4,716,897 | A | 1/1988 | Noguchi et al. |
| 4,788,977 | A | 12/1988 | Farin et al. |
| 4,818,954 | A | 4/1989 | Flachenecker et al. |
| 4,832,048 | A | 5/1989 | Cohen |
| 4,844,063 | A | 7/1989 | Clark |
| 4,919,129 | A | 4/1990 | Weber, Jr. et al. |
| 5,007,257 | A | 4/1991 | Thompson |
| 5,087,257 | A | 2/1992 | Farin et al. |
| 5,152,762 | A | 10/1992 | McElhenney |
| 5,241,242 | A * | 8/1993 | Daub ................ H05B 41/2921 315/127 |
| 5,312,401 | A | 5/1994 | Newton et al. |
| 5,334,198 | A | 8/1994 | Hart et al. |
| 5,531,676 | A | 7/1996 | Edwards et al. |
| 5,688,269 | A * | 11/1997 | Newton ............. A61B 18/1233 606/35 |
| 5,769,841 | A * | 6/1998 | Odell ................. A61B 18/1206 606/1 |
| 5,808,470 | A * | 9/1998 | Adams, III .......... G01R 31/025 324/509 |
| 6,494,877 | B2 | 12/2002 | Odell et al. |
| 7,358,720 | B1 * | 4/2008 | Maier .................. G01D 5/2013 324/207.26 |
| 7,422,589 | B2 | 9/2008 | Newton et al. |
| 7,465,302 | B2 | 12/2008 | Newton et al. |
| 8,007,494 | B1 | 8/2011 | Taylor et al. |
| 2001/0056279 | A1 | 12/2001 | Odell et al. |
| 2002/0140433 | A1 | 10/2002 | Lawson et al. |
| 2003/0169544 | A1 | 9/2003 | Langford et al. |
| 2004/0030328 | A1 * | 2/2004 | Eggers ............... A61B 18/1206 606/34 |
| 2005/0212526 | A1 | 9/2005 | Blades |
| 2006/0041253 | A1 * | 2/2006 | Newton ............. A61B 18/1233 606/32 |
| 2006/0181820 | A1 * | 8/2006 | Elms ...................... H02H 3/331 361/42 |
| 2006/0195733 | A1 | 8/2006 | DeHaven |
| 2007/0058304 | A1 | 3/2007 | Parker et al. |
| 2007/0129716 | A1 | 6/2007 | Daw et al. |
| 2008/0082095 | A1 * | 4/2008 | Shores ............... A61B 18/1206 606/34 |
| 2009/0112204 | A1 | 4/2009 | Aronow et al. |
| 2009/0174981 | A1 | 7/2009 | Mallon et al. |

OTHER PUBLICATIONS

Schneider, Laura, "Response to US Office Action re U.S. Appl. No. 13/786,670", filed Sep. 17, 2015, p. 9, Published in: US.
Shay, David M., "US Office Action re U.S. Appl. No. 08/895,038", filed May 12, 2009, p. 37, Published in: US.
Landry II, Gerald Ernest, "Office Action re U.S. Appl. No. 12/257,562", filed Aug. 20, 2012, p. 28, Published in: US.
Shay, David M., "US Office Action re U.S. Appl. No. 08/895,038", filed Mar. 28, 2007, p. 28, Published in: US.
Shay, David M., "US Office Action re U.S. Appl. No. 08/895,038", filed May 20, 1998, p. 5, Published in: US.
Shay, David M., "US Office Action re U.S. Appl. No. 08/895,038", filed Sep. 10, 2007, p. 4, Published in: US.
Hakim, Toni, "US Office Action re U.S. Appl. No. 08/895,038", filed Oct. 22, 2007, p. 2, Published in: US.
Shay, David M., "US Office Action re U.S. Appl. No. 08/895,038", filed Oct. 25, 2000, p. 6, Published in: US.
Landry II, Gerald Ernest, "Office Aciton re U.S. Appl. No. 12/257,562", filed Oct. 19, 2011, p. 9, Published in: US.
Neugeboren, Craig, "Response to Office Action re U.S. Appl. No. 12/257,562", filed Feb. 12, 2013, p. 14, Published in: US.
Neugeboren, Craig, "Response to Office Action re U.S. Appl. No. 12/257,562", filed Apr. 10, 2012, p. 7, Published in: US.
Godward, Cooley, "Response to Office Action re U.S. Appl. No. 08/895,038", filed Mar. 12, 2002, p. 6, Published in: US.
Robinson, Eric J., "Response to Office Action re U.S. Appl. No. 08/895,038", filed Mar. 26, 2002, p. 8, Published in: US.
Craig Neugeboren, "Response to Office Action re U.S. Appl. No. 08/895,038", filed Jul. 6, 2007, p. 5, Published in: US.
Hafer, Deborah, "Response to US Office Action re U.S. Appl. No. 08/895,038", filed Mar. 12, 2002, p. 1, Published in: US.
Neugeboren, Craig, "Response to Office Action re U.S. Appl. No. 08/895,038", filed Oct. 17, 2007, p. 14, Published in: US.
Neugeboren, Craig, "Response to Office Action re U.S. Appl. No. 08/895,038", filed Oct. 25, 2007, p. 5, Published in: US.

* cited by examiner

MULTIPLE PARAMETER FAULT DETECTION IN ELECTROSURGICAL INSTRUMENT SHIELDS

PRIORITY AND RELATED APPLICATIONS

This application is a continuation of U.S. patent application Ser. No. 13/786,670 filed Mar. 6, 2013 and entitled "Multiple Parameter Fault Detection in Electrosurgical Instrument Shields," which is a divisional application of and claims the benefit of U.S. patent application Ser. No. 12/257,562 filed on Oct. 24, 2008, which claims the benefit of Provisional U.S. Patent Application No. 60/982,990 filed on Oct. 26, 2007. The details of application Ser. Nos. 13/786,670, 12/257,562 and 60/982,990 are incorporated by reference into the present application in its entirety and for all purposes.

FIELD OF THE INVENTION

Aspects of the present invention relate to devices and methods for the detection of faults in electrosurgical instruments powered by electrosurgical units (ESU). More particularly, aspects of the present invention relate to the monitoring and use of multiple radio frequency parameters in order to more particularly and specifically control the delivery of electrosurgical current during a surgical procedure.

BACKGROUND

The method used in predicate systems for detecting faults in the shields of electrosurgical instruments is sensitive only to the current in the shield. Furthermore, existing systems rely heavily on analog circuits and associated monitoring techniques that result in limitations in how the existence of a shield fault is detected, communicated to a user, and delivered to the ESU for deactivation. Examples include devices and methods such as those disclosed in U.S. Pat. Nos. 5,312,401 and 5,688,269, commonly assigned with the present application to Encision, Inc. of Boulder, Colo.

Figure 1:
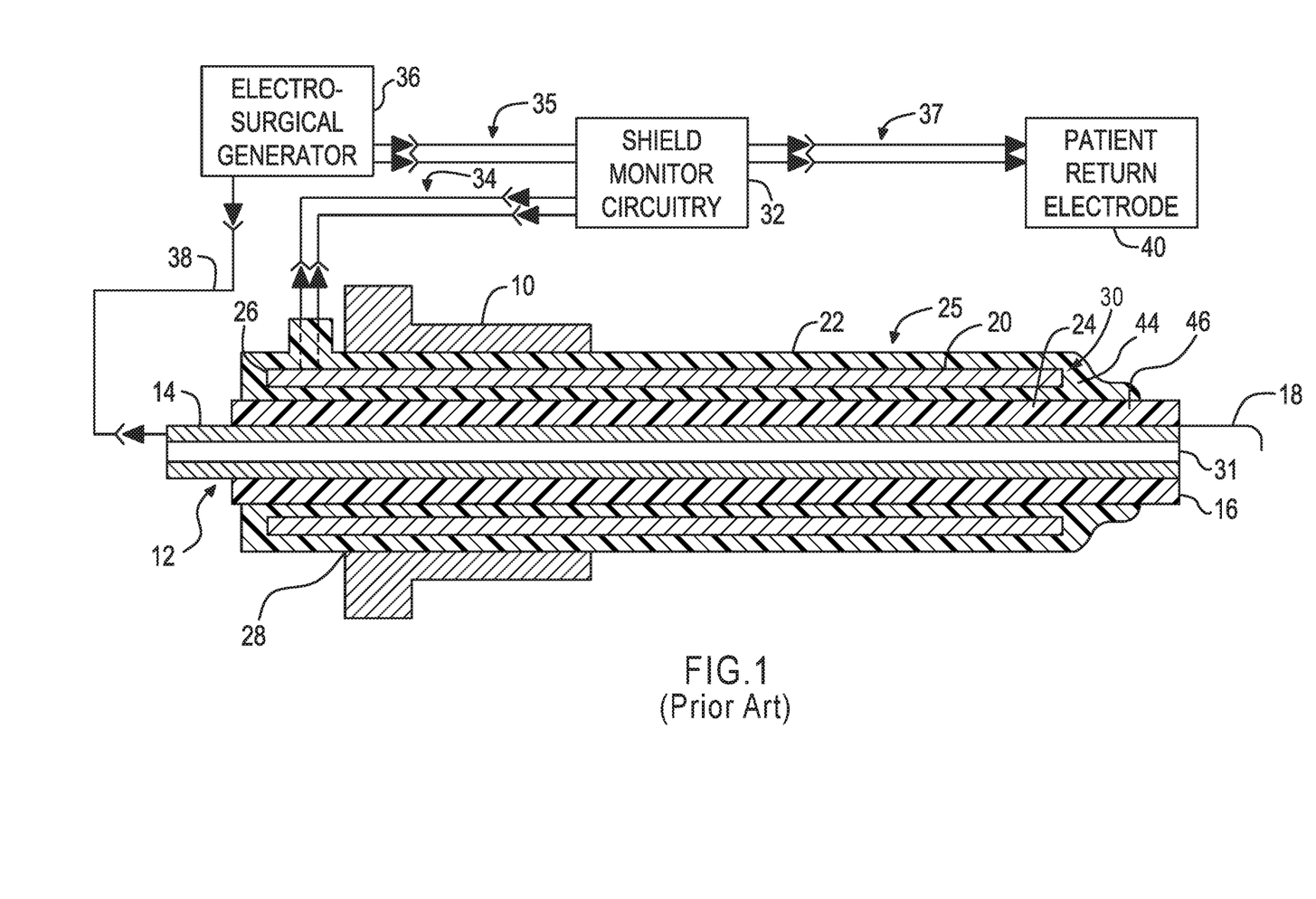
FIG. 1 is a representative example of a prior art electrosurgical tool and shield monitoring circuitry.

Illustrated in FIG. 1 is an example of a laparoscopic electrosurgical apparatus as is known in the prior art. A tubular safety shield assembly 25 includes a tubular shield 20 having a layer of insulation 22 provided on the outer surface thereof and an optional layer of insulation 24 provided on the inner surface thereof. The tubular shield assembly is inserted through trocar sheath 10 to thereby provide a passageway through which the active electrode probe 12 may be inserted. An elongated port 31 may extend through the active electrode through which irrigation fluids, suction, a pressurized gas stream, etc. may pass. When active probe 12 and tubular shield assembly 25 are in their respective inserted positions as shown in FIG. 1, the shield 20 surrounds the active probe from at least (a) a proximal point 26 prior to the entry point 28 of the active probe into the trocar sheath 10 to (b) a distal point 30 in proximity to the tip 18 of the active probe.

Shield monitor circuitry 32 is connected to shield 20 via a dual conductor lead 34 whereby the integrity of the connection of the shield to the monitor circuitry can be monitored.

The active electrode probe 12 is connected to an electrosurgical generator 36 via an active lead 38. The electrosurgical generator is connected to a patient return electrode 40, via the shield monitor circuitry 32 and, in particular, the return terminal of the generator is connected to circuitry 32 via lead 35 while the circuitry 32 is connected to the return electrode via lead 37. Upon detection of a fault condition by the shield monitor circuitry, the electrosurgical generator 36 may be deactivated by opening a relay in the connection between the generator and patient return electrode 40 although other means may also be employed to deactivate the generator.

As can be appreciated by those of skill in the art, the prior art as described herein only provides the ability to detect a fault condition based on sensing the current in the shield and thus does not provide a great deal of flexibility to the surgeon to account for the use of modern electrosurgical instruments and varying surgical procedures that might benefit from a monitoring device that is capable of detecting faults based on other radio frequency parameters. Such benefits may include earlier fault detection of or detection of a fault at lower ESU power settings. In addition, the limitations imposed by the use of analog sensing electronics and associated processing schemes make more sophisticated monitoring techniques difficult and make it more difficult to customize the fault detection process for varying situations where one fault threshold may not be adequate or appropriate.

SUMMARY OF THE INVENTION

In accordance with one aspect a system for detecting faults within an electrosurgical instrument comprises monitoring circuitry coupled to an electrosurgical generator and an electrosurgical instrument wherein the monitoring circuitry is adapted to measures at least two of active voltage, active current, and shield current.

In accordance with another aspect, a system for detecting faults within a shielded electrosurgical instrument, comprises an electrosurgical generator coupled to an electrosurgical instrument and adapted to deliver power through the electrosurgical instrument. Monitoring circuitry is coupled to the electrosurgical generator and the electrosurgical instrument. The monitoring circuitry comprises structure for detecting a resistance fault in the electrosurgical instrument, structure for detecting at least one current fault in the electrosurgical instrument, structure for a detecting a capacitance fault in the electrosurgical instrument, and structure for detecting a power fault in the electrosurgical instrument. The monitoring circuitry is adapted to contemporaneously detect at least two of the resistance fault, high-current fault, low-current fault, capacitance fault, and power fault.

Other aspects and features are contemplated and are more fully described in the following description and as would be known to one of skill in the art.

BRIEF DESCRIPTION OF THE DRAWINGS

Various objects and advantages and a more complete understanding of the present invention are apparent and more readily appreciated by reference to the following Detailed Description and to the appended claims when taken in conjunction with the accompanying Drawings, wherein:

DETAILED DESCRIPTION

While the prior art has been described in the context of a rigid laparoscopic instrument, it should be understood that aspects of the present invention may be utilized in conjunction with a variety of types and designs of shielded surgical instruments and other tools. For example, electrosurgical instruments employing flexible tubing and those instruments utilizing a generally larger diameter tubular shaft, such as hysteroscopic instruments described in e.g. U.S. Pat. No. 7,422,589, commonly assigned to Encision, Inc., may also be used in conjunction with aspects of the present invention. U.S. Pat. No. 7,422,589 describes alternative referencing for the instrument shield connection other than a direct connection to the return electrode. Such connections are possible for each of the measuring techniques described herein.

In general terms, aspects of the present invention relate to an improved method of detecting faults in, for example, the shields of electrosurgical instruments. In one embodiment, a device constructed in accordance with aspects of the invention relies on a combination of different radio frequency parameters of the electrosurgical instrument in order to detect a variety of faults that might occur in the instrument. These parameters can include one or more of the following:
1. Average, real power in the shield;
2. Root mean square (RMS) of the real part of the shield current;
3. RMS of the total current in the shield;
4. RMS of the total current in the shield below a certain active electrode voltage (referenced to the return electrode);
5. Magnitude of the impedance or capacitance between the active ESU electrode and the shield;
6. Resistance between the active ESU electrode and the shield; and/or
7. Active electrode voltage (referenced to the return electrode) in combination with other parameters.

For the faults generated in systems using higher electrosurgical unit ("ESU") power settings, the average, real power consumed in the shield is preferably used to detect a fault condition when the resistance is still relatively high between the active electrode and its shield. Although it may be more difficult, but not impossible, to calculate, the RMS of the real part of the shield current can be used as an alternative. As arcing occurs between the active electrode and the shield, a significant amount of real power begins to be consumed (as opposed to imaginary power from the normal capacitive coupling between the active and the shield). As more of a carbonized and conductive pathway develops between the active electrode wire and the shield, the amount of real power consumed in the insulating shield increases to some relatively high point (such as generator peak power) based on the ESU and the patient load. A trip point is set so that if more than a certain amount of power (e.g. in Watts) is consumed for a minimum of a certain length of time, a fault is detected and latched in one or more types of internal logic. The average real power in the shield can be found by multiplying a measure of the active electrode voltage by a measure of the shield current in real time and taking the average over frames covering a sufficient period of time (e.g., 30 μs to 300 ms). These frames may be overlapping although in simple implementations overlapping frames are not required. The power fault condition can be measured reliably when the voltage and current are above defined minimums such as 30 V and 50 mA. Shield current need not be measured directly. In a monopolar electrosurgical system a measurement of the return electrode current may be subtracted from a measurement of the current through the active electrode to yield the shield current. Also, the active electrode voltage and/or shield current may need to be above some minimum threshold values so that the inherent noise in measuring these does not cause a false determination of a fault.

As an alternative to using average real power in the shield for the primary fault detection, the real portion of the shield current may also be used. Since the shield current is normally capacitive, as the shield current develops a significant real part, it likely contains at least a partial short circuit to the active electrode. In calculating the RMS of the real part of the shield current, the phase difference between either the active electrode voltage or current and the shield current is taken into account.

For the typical fault at lower ESU power settings, resistance between the active ESU electrode and the shield may be used. Sufficient active electrode voltage may not exist to trip a power fault. However, the resistance may be low enough to trip a resistance fault. At higher ESU power settings, for a given, moderate amount of resistance between the active ESU electrode and the shield, a power fault may trip and not a resistance fault. Also, the active electrode voltage, shield current, and/or shield power must be above some minimum threshold values so that the inherent noise in measuring these does not cause a false determination of a fault.

If the resistance between the active electrode and the shield gets small enough, the amount of real power consumed in the shield will actually decrease. However, the amount of shield current will continue to increase. So another fault condition is tripped when the RMS current in the shield exceeds a certain amount. This RMS current fault can occur even when the active electrode voltage is below the minimum threshold value that may be necessary for power or resistance faults. A fault condition could be caused by an arc over a sufficient period of time or if a shield simply short circuits to an active electrode wire. Such a fault condition may progress over time from a higher to a lower resistance between the active electrode and the shield. It is desirable to detect these faults as soon as practical for patient safety and electrosurgery efficacy. For example, the arc could develop by continuing to re-key the faulty instrument after a fault was detected.

As used herein, the term active voltage is meant to refer to the voltage as measured from the active electrode to the return electrode.

As used herein, the term active current is meant to refer to either the current into the active electrode or back from the return electrode into the active electrode monitor.

As used herein, the term shield current is meant to refer to the total shield current.

Figure 2:
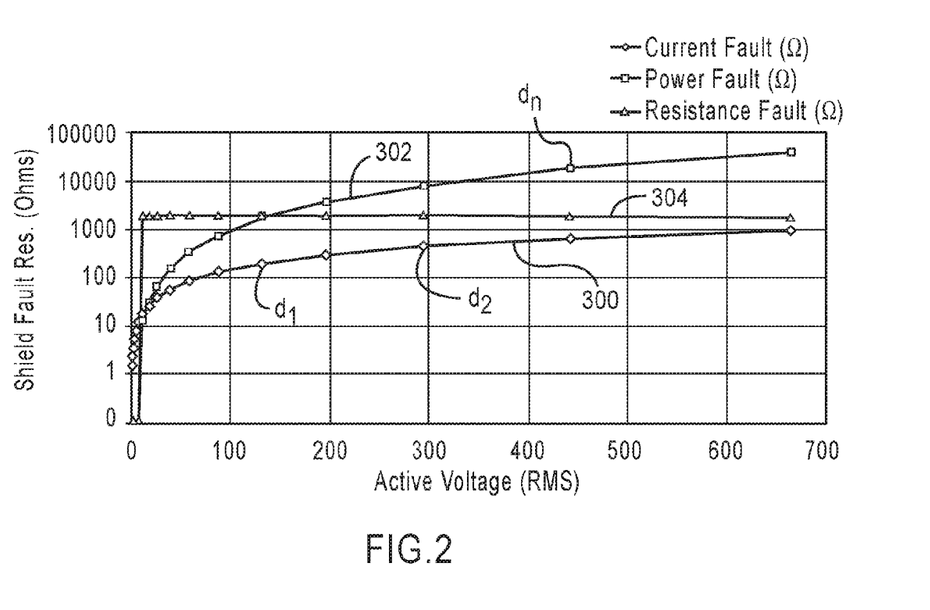
FIG. 2 is a graph showing the range of fault conditions that may be utilized in accordance with devices constructed in accordance with aspects of the present invention.

FIG. 2 shows one scenario for how the current, power, and resistance fault detection methods are all useful depending on the resistance of the shield fault and the active electrode voltage. In FIG. 2, each of the data points $d_1$, $d_2$, $d_n$, etc, indicated in the graph represent a specified trip point corresponding to either a current monitoring scheme 300, a power monitoring scheme 302, or a resistance monitoring scheme 304. In practice, any point along the curve depicted in FIG. 2 may be utilized as a potential trip point defined within the monitoring system. Note that a rapid decrease in the resistance between the shield and the active electrode may allow more than one type of fault to trip in the same frames simultaneously.

With monitoring circuitry constructed in accordance with aspects of the present invention, a wide range of potential fault conditions are capable of being programmed into the circuitry. Different fault conditions may be set in the monitor to correspond to the use of various electrosurgical instruments, various surgical procedures, or other specific surgical conditions that would warrant more precise control over when, and to what extent, the monitor will shut off the flow of power to the electrosurgical instrument. In FIG. 2, the examples shown represent one embodiment where the resistance trip is set at 2 k$\Omega$, a power trip is set at 10 W and a current trip is set at 650 mA. In these examples, the minimum voltage for resistance trips is set at 30V and the minimum current for current trips was set at 50 mA. As mentioned above, different surgical scenarios may warrant the use of different trips conditions and ranges. Devices constructed in accordance with aspects of the present invention are capable of accommodating these specific surgical requirements.

Figure 6:
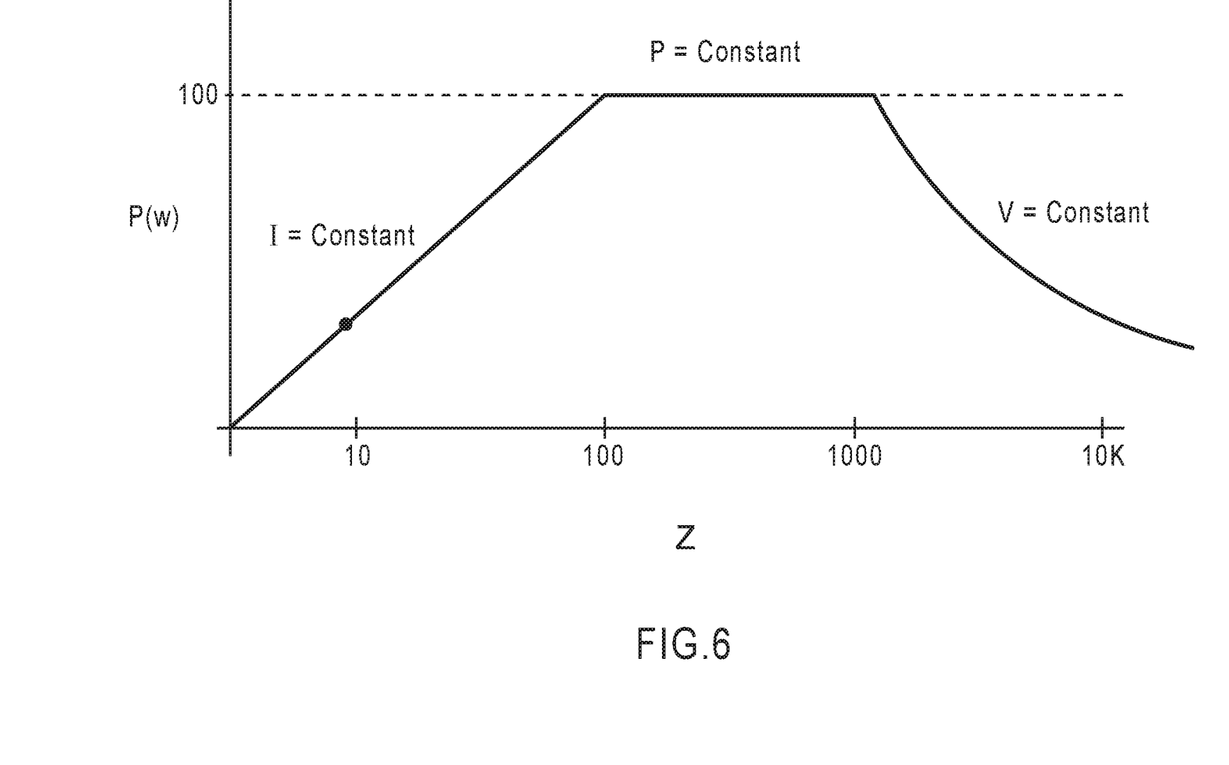
FIG. 6 is a graph showing typical load characteristics of an electrosurgical generator.

An intermediate condition occurs when the shield power is very low (due to a near short circuit between the active and shield wires, and therefore difficult to measure for a resistance fault) but the ESU power setting is too low to trip a current fault. FIG. 6 illustrates the conditions under which this scenario occurs showing the various current constant, power constant and voltage constant condition ranges. In this case, yet another programmable condition is provided in which a fault is tripped when the RMS current exceeds a threshold (e.g., 200-1000 mA) as long as the active voltage is less than a threshold level (e.g., 150V RMS). It may be useful to have several of such conditions based on shield current at different levels of active electrode voltage. The additional current fault condition(s) complements the other conditions so that instrument faults are detected sooner. Some classes of instruments (such as hysteroscopic) may require a different length or number of frames over which to average the fault parameters to prevent false-positive trips or for increased sensitivity to possible fault conditions. Therefore, it useful to have programmable settings for the length or number of frames over which the fault parameters are averaged. These settings can be based on the class of instrument or the electrosurgical conditions actually present.

If the shield wire is not connected to its reference potential, then the normal capacitive current in the shield may be far too small. This condition is dangerous because the shield cannot function properly in the case of a breakdown of insulation between the active and shield wires. However, in this case, the complex impedance of the shield (as seen from the active electrode) is high. So another fault condition is tripped when the magnitude of the impedance of the shield is too high. This condition can only be measured reliably when the active electrode voltage is above a certain minimum (e.g., 15V).

All of these fault conditions may be connected together by one or more relationships implemented in hardware or software logic (e.g. an OR condition in an FPGA logic chip). The combinatorial logic includes provisions for the defined ranges of accuracy for each of the conditions. If any of these fault conditions is detected, the power to the surgical instrument is reduced or disabled temporarily or permanently.

Figure 3:
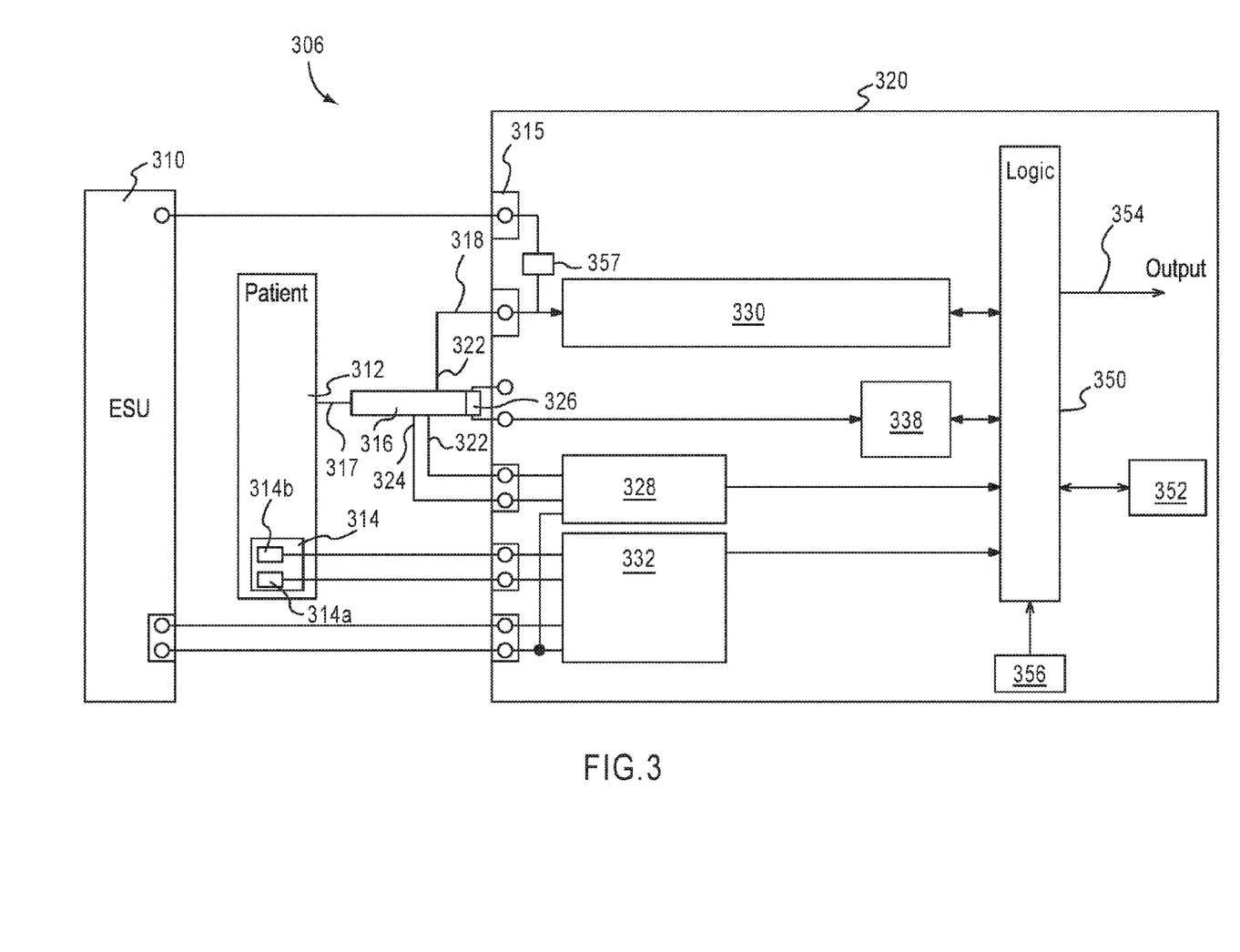
FIG. 3 is a block diagram of an embodiment in accordance with aspects of the present invention.

FIG. 3 shows a generalized block diagram of one possible embodiment of a monitoring system 306 constructed in accordance with aspects of the present invention. It should be understood that the representation shown in FIG. 3 is meant to show the main components of such a system on a general level. In practice, and in any physical embodiment of a device that falls within the spirit and scope of the present invention, the individual components depicted in FIG. 3 may take one of many forms, may be integrated with one another, or may be located in physically distinct locations. By representing aspects of the present invention in accordance with the figures, and particularly FIG. 3, it is in no way meant to limit the scope of the invention.

During an electrosurgical procedure, patient 312 is fitted with a return electrode pad 314 comprised of dual return electrodes 314a and 314b. Electrosurgical apparatus 316 includes an active electrode tip 317 that includes one or more types of end effectors such as graspers, ablation devices, scissors, and various other tools known in the art, and delivers electrosurgical power through the active electrode tip 317. Electrosurgical apparatus is preferably configured as described above in conjunction with FIG. 1 but may take various other forms as known in the art. The electrosurgical apparatus 316 includes a shield that is monitored by the system 306. Conductive leads 318, 322 and 324 connect the shield and the electrosurgical apparatus 316 to the monitoring circuitry 320 in accordance with known methods, such as those disclosed in commonly assigned U.S. Pat. Nos. 5,312,401, 5,688,269, and 5,769,841, the details of which are incorporated by reference in their entirety and for all proper purposes. Examples of electrosurgical apparatus 316 include laparoscopic tools, hysteroscopy tools, surgical tools with rigid and flexible shafts, remote and robotically controlled surgical instruments, and instruments used for any number of other surgical procedures that might utilize electrosurgical current and associated techniques.

In FIG. 3, different sensing apparatus are used to individually sense the active voltage, the active current and the shield current from the electrosurgical apparatus 316. In FIG. 3, sensor 332 senses active current, sensor 330 senses active voltage, and sensor 328 senses the shield current. In one embodiment, the sensors may comprise differential capacitive dividers, filters, op amps, and/or analog-digital converters (ADCs). The sensors are preferably configured to contemporaneously or simultaneously sense the active voltage, active current, and shield current. In some embodiments, the active current is used as a means of recording and or displaying power and current delivered to the patient and may or may not be used for fault detection.

The sensors 328, 330 and 332 pass the monitored shield current, active current, and the active electrode voltage to a processor 350. In one embodiment, the processor 350 comprises a field programmable gate array (FPGA) and acts in concert with a memory element 352 (such as an EEPROM), and an oscillator 356. An output 354 of the processor 350 passes visible and/or audible indications of the monitor status to a surgeon, operator or other user.

An identification element 326 is coupled to its own sensing element 338 and the processor 350, and provides a variety of customizable features to the monitoring system 320. In one embodiment, the identification element 326 is a resistor identification device that tells the processor 350 what type of conditions should be employed in the sensing process. In general terms, the monitor 320 can measure the resistor 326 and accordingly define the instrument class within the processor. For example, a low resistance may indicate a standard electrosurgical instrument classification, while a high resistance may indicate devices used in hysteroscopy. Different instruments (and/or instrument cords)

are recognized through different identification (ID) resistors 326. As new instruments are developed, additional fault thresholds can be programmed into the monitor without significant hardware modification as the processor and monitor itself will obtain this information from the identification resistor 326. Other types of instrument identification may also be used, such as bar codes/scanners and other identification techniques known in the art. The identification element may be incorporated into the instrument 316 itself or may reside as a separate input to the monitor 320. The representation in FIG. 3 is meant to include each of these embodiments.

Other methods of instrument identification are contemplated. One method uses two separate pins in the instrument connector on the monitor (See e.g. 510 in FIG. 4). An identification resistor is attached to these pins in the mate to the 512 connector (which may be attached to the cord of the electrosurgical instrument). This method has the advantage of simplifying the electronic design inside the monitor required to identify the resistance. With this method, different instrument cables are required for each class of electrosurgical instrument so that the distal end of the cable can be made so that it is compatible only with the intended class.

A second method puts the identification resistor inside the connector for the instrument itself where it plugs into the instrument cable. In this case, the identification resistor is attached across the two shield wires. In some embodiments, it may be useful to place a diode and a capacitor in parallel with the resistor in this case. The diode allows checking the integrity of the shield connections, while the capacitor prevents excessive voltage from developing across the resistor. This method has the advantage of allowing the same instrument cables to be used for all classes of instruments.

In general terms, if a fault is detected, a relay 357 will interrupt power to the foot-switched electrode output independently of what the ESU is doing. In the embodiment where active voltage is sensed with a differential capacitive divider, this is used as a way to minimize the additional active electrode load (and leakage). In an embodiment where the processor 350 includes an FPGA, this logic circuit may calculate fault conditions over some non-overlapping time frame, for example, 1.52 ms time frames. Additional active voltage and current sensing can be used along with multiplexers into low-pass filters (or as separate circuits) to monitor hand-switched monopolar electrode output(s) and/or bipolar electrode outputs in a similar fashion.

Figure 4:
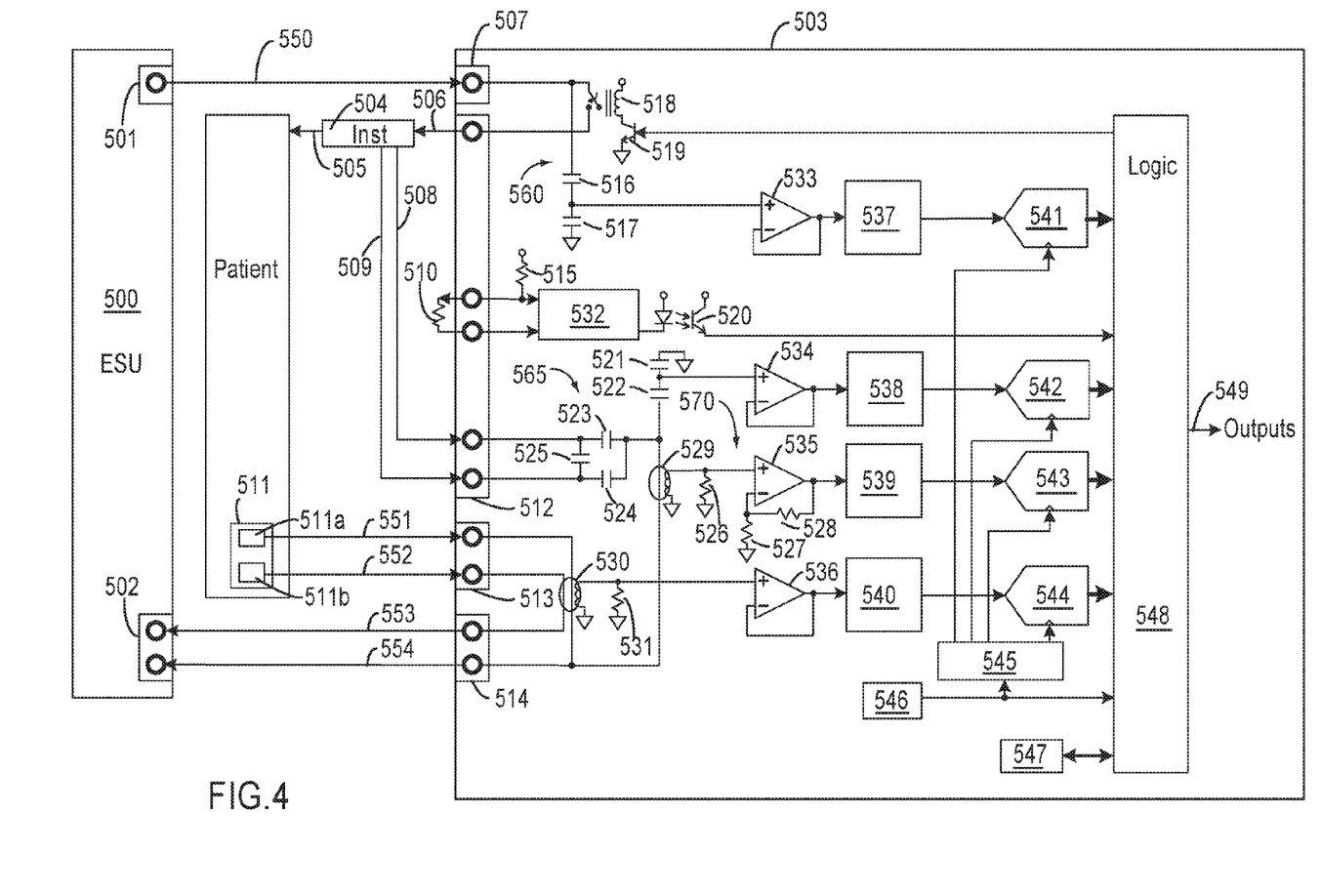
FIG. 4 is another embodiment of a monitoring system in accordance with aspects of the present invention.

FIG. 4 depicts a more specific embodiment of the monitoring system 503 described above. Electro surgical generator 500 includes a jack or other type of connector 501 for a foot switched monopolar active electrode output and a jack or other type of connector 502 for a patient return electrode. In some embodiments, the jack 502 includes dual patient contacts compatible with the contact quality management (CQM) system used in many known and generally available ESUs. The monitoring system 503 is coupled to the combination of an ESU 500, a patient, and an instrument that includes a shielded active electrode 504, an active electrode end effector or tip 505 that conducts electrosurgical current to the patient. Conductor 506 connects the shielded active electrode 504 to a connector 507 on the monitor 503. Connector 507 is for the foot-switched monopolar electrode output on the monitor 503. In one embodiment connector 507 is contained within the monitor 503 so that cable 550 emerges from a front panel of the monitor 503. Shield conductors 508 and 509 connect the shielded active electrode 504 to a connector 512 on the monitor 503.

A CQM compatible patient return electrode 511 includes first 511*a* and second 511*b* patient contact pads which are connected via conductors 551 and 552 to contact jack 513 on the monitor 503.

In one embodiment, the foot switched active electrode voltage (relative to the return electrode voltage) is measured using two capacitor dividers referenced to circuit ground. The first capacitor divider 560 measures the active electrode voltage relative to circuit ground, and the second capacitor divider 565 measures the return electrode voltage relative to circuit ground. In one embodiment, a first capacitor 516 for the first capacitor divider 560 has a nominal value of approximately 8 pF, is rated to approximately 18 kV, and is formed from a temperature compensated dielectric, for example ceramic COG. In one embodiment, capacitor 516 is formed by placing several individual capacitors in series (e.g. six 47 pF, 3 kV COG capacitors) thereby allowing the creation of an economical, safe capacitor with a suitable high-voltage rating and suitably low capacitance. In addition, by utilizing capacitors in series, if one of the capacitors in the series were to fail, the remaining series capacitors would still have a sufficiently high rating to handle the voltage between the active electrode and circuit ground. The first capacitor divider structure 560 also includes a second capacitor 517 used to measure the foot-switched active electrode voltage. In some embodiments, capacitor 517 has a temperature compensated dielectric and may be rated as a 22 nF, 50V COG capacitor. The second capacitor divider structure 565 is formed from capacitors 522 and 521. In some embodiments, capacitor 522 has similar characteristics to capacitor 516. Capacitor 521 has similar characteristics to capacitor 517.

A reed relay 518 controls the foot-switched active electrode 504. In one embodiment, the relay 518 is a Coto 5501-12-1 with a 10 kV peak dielectric rating between the coil and the contacts, a 7500V rating across the contacts, and a contact rating of 5 A. A transistor 519 used to drive the coil of the relay controlling the foot-switched active electrode. Transistor 519 is preferably controlled by the programmable logic 548.

Op amp buffer 533 is preferably a high-speed operational amplifier op amp (e.g. a 145 MHz gain-bandwidth product) with a low input bias current such as made by Analog Devices, model number AD8065. Filter 537 is coupled to the op-amp 533. Filter 537 may include a one-pole, 1 kHz high pass and a two-pole, 9.8 MHz low pass filter in series. Preferably, this two-pole low pass filter is matched with the two-pole low pass filter 538 described below. Analog digital converter (ADC) 541 couples with the buffered, divided, filtered active electrode voltage. In one embodiment, ADC 541 has a 12-bit parallel output and operates at 20 megasamples per second. For example, as embodied in one half of a Linear Technology LTC2291 dual ADC. ADC 541 couples to a logic element 548. Logic element 548 is described in further detail below.

Capacitors 523 and 524 are in series with the two wires 508 and 509 connected to the shield for the active electrode 504. Capacitors 523 and 524 prevent direct current (DC) from flowing back to the patient return jack of the ESU 500. Capacitors 523 and 524 are sufficiently large that they have no significant voltage across them during normal operation. Nominally, and in some embodiments, capacitors 523 and 524 are 10 nf, 3 kV, Y5U ceramic capacitors. Capacitor 525 can be placed across the wires connected to the shield for the active electrode to reduce the voltage that can develop between these two wires. In one embodiment capacitor 525 is a 100 nF, 50V, X7R ceramic capacitor.

Current transformer 529 is used to measure the current in the two shield wires 508 and 509. In one embodiment, current transformer has a 1:30 turns ratio and has an air core. Termination resistor 526 is coupled to the current transformer 529. In one embodiment, termination resistor 526 is a 10 ohm resistor. An op amp circuit 570 buffers and amplifies the signal from the current transformer 529. Op amp circuit 570 includes the op amp 535 and resistors 527 and 528. Op amp 535 is similar to op amp 533 described above. Resistor 527 (1 k-ohms in one embodiment) is connected between circuit ground and the inverting input to op amp 535. Resistor 528 (499 ohms in one embodiment) is connected between the 535 op amp output and its inverting input. The combination of resistor 527 and resistor 528 allows a voltage gain of greater than 1 in this op amp circuit. In one embodiment, the voltage gain is approximately 1.5. Filter 539 couples to the buffered, current transformed shield current and is similar to filter 537 described above. ADC 543 couples to the filter 539 and is similar to ADC 541 described above. ADC 543 couples to logic element 548.

Op amp buffer 534 is coupled to the capacitor divider structure 565 defined by capacitors 521 and 522. Op amp buffer 534 is similar to op amp 533 described above. Filter 538 is couple to the buffered, divided patient return electrode voltage and is similar to filter 537 and 539 described above. ADC 542 couples to the filter 538 and is similar to ADCs 541 and 543 described above. ADC 542 couples to logic element 548. It is desirable that filters 537 and 538 match each other well to allow an accurate calculation of the voltage between the active and return electrodes by subtracting the voltages measured by ADCs 541 and 542.

Current transformer 530 is used for measuring the current in the two patient return electrode wires 551 and 552. Current transformer 530 has a 1:30 turns ratio and an air-core in one embodiment. Current transformer 530 is coupled with a termination resistor 531 that in one embodiment is a 10 ohm resistor. Op amp 536 couples to the transformer-coupled current from the patient return electrode. Op amp 536 is the same type of op amp as 533 described above. Filter 540 couples to the op amp 536. In one embodiment, filter 540 is the same as filter 537 described above. ADC 544 is coupled to filter 540 and in turn couples to the logic element 548. ADC 544 is similar to ADC 541 described above.

Connector 514 on active electrode monitor 503 is used for the cable going to the ESU's jack for the patient return electrode 502. This connector is alternatively inside the active electrode monitor 503 so that the cable going to jack 502 for the patient return electrode is formed as a pigtail emerging from the front panel of the active electrode monitor. Conductors 553 and 554 are in one embodiment contained in a cable going from the ESU's patient return electrode jack 502 to connector 514 on the active electrode monitor.

An identification (ID) resistor 510 is associated with the class of the shielded active electrode 504 and can be in one of the connectors for the shielded active electrode cable or in the shielded active electrode itself. The resistance of the ID resistor 510 identifies the class of electrosurgical instrument in use. In one embodiment, the ID resistor 510 is in a connector that plugs into the monitor 503 on the cable to the shielded active electrode 504. This type of implementation requires the cable to the shielded active electrode to be compatible with only the intended class of shielded active electrode. In one embodiment, identification circuit 532 includes, for example, window-comparators arranged in parallel along with a small programmable logic device and 1-MHz crystal oscillator. Circuit 532 may thus create a repetitive digital, serial output data stream containing the number of the ID resistor (if one is plugged in). Alternative circuits could use an analog-digital converter instead of the window comparators as well as a different communication arrangement with the logic element 548. In one embodiment. pull-up resistor 515 is connected to a reference voltage on one side and to the ID resistor 510 on the other side. The combination of the pull-up resistor 515 and the ID resistor 510 form a resistor divider with an output voltage dependent on the value of the ID resistor. Opto-isolator 520 is used to convey the identification number of the resistor 510 to the logic element 548. In one embodiment, opto-isolator 520 is an Optek OPI1264C and allows the active electrode ID resistor to be near the voltage potential of the shield wires (which are near patient return voltage when a fault is not occurring). In this embodiment, the opto-isolator 520 has a 10 kV isolation voltage rating.

Low-skew buffer 545 allows the ADCs 541-543 to be clocked at essentially the same time. In one embodiment buffer 545 utilizes an On Semiconductor NB3L553. The oscillator element 546 may be formed from the combination of a 40-MHz oscillator followed by a D-type flip-flop configured for a divide-by-two operation. The output is then a 20-MHz square wave with very close to a 50% duty cycle. Electrically-erasable, programmable read only memory (EEPROM) 547 may be configured in one embodiment as 1024×16 bits with a serial port interface (SPI). EEPROM 547 may hold the all of the configuration settings for the various classes of electrosurgical instruments along with calibration data for the active electrode monitor 503.

Field-programmable gate array (FPGA) 548 contains the digital logic for the active electrode monitor. This FPGA is in one embodiment a Xilinx XC3S250E. The configuration program for the FPGA may be stored in a separate non-volatile Flash memory (not shown).

Outputs 549 from the FPGA include in some embodiments an input to a speaker-amplifier for audio output for the active electrode monitor. Other FPGA outputs may drive visual front and rear panel indicators on the monitor 503. The FPGA 548 may also interface with a universal serial bus (USB) port for factory calibration and one or more remote displays.

As one alternate embodiment to that shown in FIG. 4, the devices monitoring the current in the patient return electrode are not utilized, namely reference numbers 530, 531, 536, 540, and 544.

Figure 5:
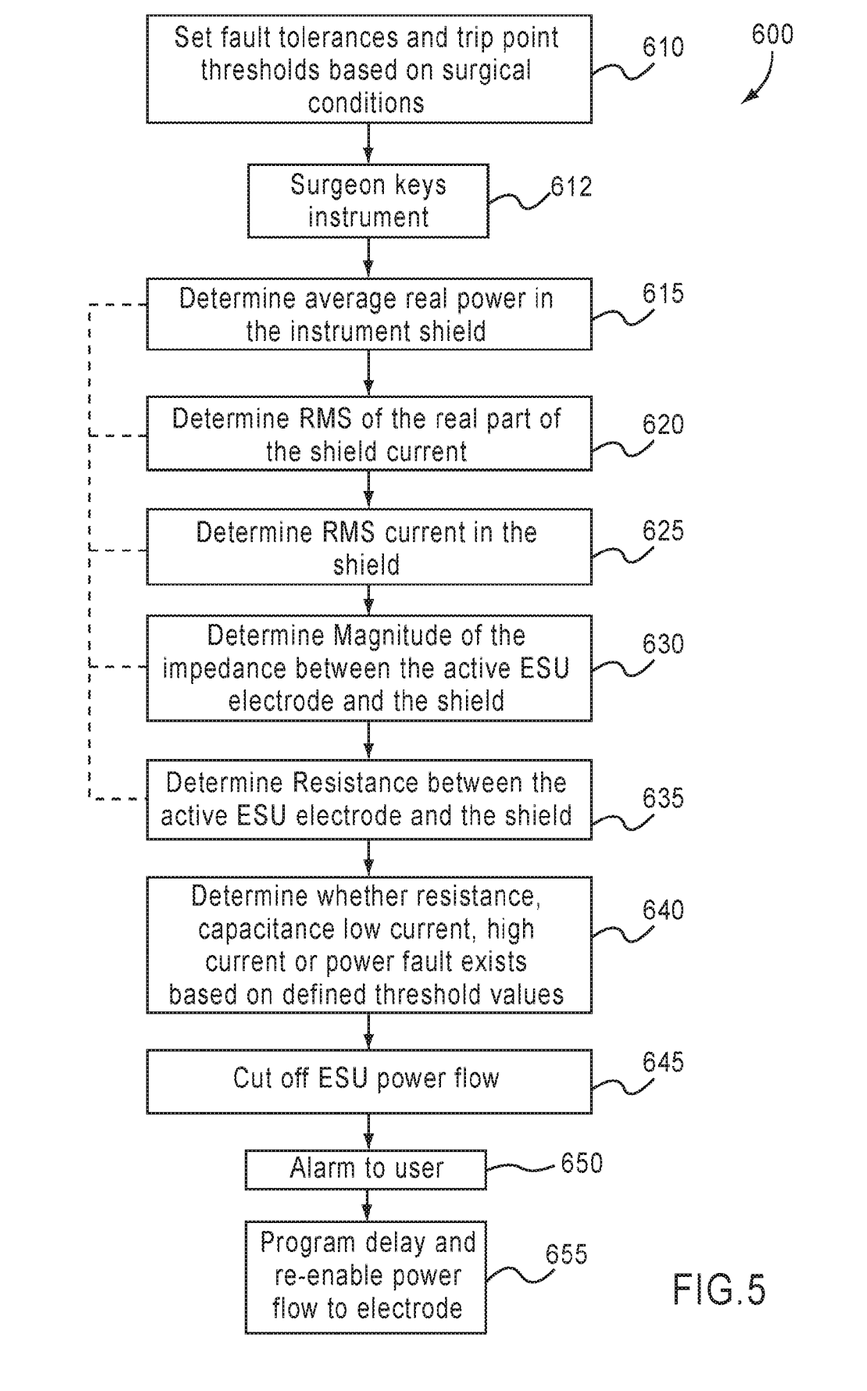
FIG. 5 is a flow chart depicting one embodiment of a process for determining fault conditions in accordance with various aspects of the present invention.

FIG. 5 depicts an exemplary method 600 implemented within a monitoring system constructed in accordance with aspects of the present invention. In one aspect, at step 610 fault tolerances and trip point thresholds are set based on specified surgical conditions. A surgeon keys or otherwise activates the power delivery at 612 and allows a voltage at electrosurgical frequencies to appear on the shielded electrosurgical instrument. The monitoring system determines the average real power in the instrument shield at step 615, determines the RMS of the real part of the shield current at step 620, determines the RMS current in the shield at step 625, determines the magnitude of the impedance between the active ESU electrode and the shield at step 630, and determines the resistance between the active ESU electrode and the shield at step 635. At step 640, based on one or more pieces of the information collected during the prior steps, the monitoring system determines whether a resistance, capacitance, power, low current, or high current fault exists by comparing the sensed values to the defined threshold values and then based on that condition determines whether to restrict or cut off power from the ESU at step 645. An alarm is then sent to the user at 650 and the system initiates a program delay prior to re-enabling power flow to the active electrode at 655. It is noted that one or more of the data gathering steps may be obtained in real time and either simultaneously or in serial fashion. Because of the FPGA's parallel processing ability, many different parameters may be monitored at the same time, providing a wide range of information for determining whether a fault condition exists. Further embodiments of fault detection processes used in the above process are described below.

In accordance with one aspect, fault conditions in the electrosurgical apparatus are detected and determined as follows. Based on the inputs sensed in the monitoring system, a processor equipped with logic circuitry may be implemented in a structure such as an FPGA (e.g. reference 350 in FIG. 3). A field-programmable gate array is a semiconductor device containing programmable logic components and programmable interconnects. Logic blocks can be programmed to perform the function of basic functions such as AND, XOR, and flip-flops or more complex functions such as decoders or multiplier functions. Many FPGAs also include blocks of separate memory. A hierarchy of programmable interconnects allows logic blocks to be interconnected as needed by the system designer. Logic blocks and interconnects can be programmed by the customer or designer, after the FPGA is manufactured, to implement any logical function and are desirable in a system constructed in accordance with aspects of the present invention since they can be programmed to implement nearly any mathematical computation and run at a very fast speed. The implementation of the logic for fault determination may be done with application specific integrated circuits (ASICs), as well as general-purpose microprocessors or those specialized for digital signal processing (DSP).

While using division as part of a fault monitoring process as described herein using an FPGA is possible, the calculations are somewhat more difficult. Thus, it is preferable, but not required, to use multiplication and addition/subtraction functions wherever possible within the FPGA or other logic circuit.

In one embodiment, a capacitance fault will be signaled if the logic circuit (e.g. an FPGA or ASIC) evaluates the following expression as true:

$$V_{active}^2 > I_{shield}^2 Z_{fault}^2$$

In another embodiment, a capacitance fault will be signaled if the logic circuit (e.g. an FPGA or ASIC) evaluates the following expression as true and where $V_{active}^2$ is greater than a minimum predetermined threshold:

$$(V_{active}^2 > I_{shield}^2 Z_{fault}^2) \text{ AND } (V_{active}^2 > V_{min}^2) \text{ AND } (I_{shield}^2 > I_{min}^2)$$

In each of the above capacitive fault determinations, the following are assumed:

$V_{active}^2$=mean, squared, active electrode voltage (over a frame)
$I_{shield}^2$=mean, squared, shield current (over a frame)
$V_{min}^2$=a constant representing the minimum level of mean, squared, active electrode voltage above which a capacitance fault may trip.
$I_{shield}^2$=mean, squared, shield current (over a frame)
$I_{min}^2$=a constant representing the minimum level of mean, squared, shield current above which a capacitance fault may trip.
$Z_{fault}^2$=a constant representing the square of the magnitude of the impedance below which a capacitance fault should be tripped. This constant may include additional scaling and may be calculated as $1/(2\pi f_{ESU} C_{fault})$ where $\pi$ is ~3.14159, $f_{ESU}$ is a nominal ESU frequency (e.g., 500 kHz), and $C_{fault}$ is the capacitance below which a fault should be tripped. Since $f_{ESU}$ can vary from less than 240 kHz to greater than 1 MHz, this method is considered to be a general check of shield connection rather than an exact threshold. This method may be more exact with more precise knowledge of the output frequency spectrum of the ESU. For example, the output frequency spectrum can be measured with a fast Fourier transform or the monitoring circuitry could receive such information directly from the electrosurgical radio-frequency generating circuitry.

In another embodiment, to avoid division calculation, a resistance fault is determined if the logic network evaluates the following expression as true:

$$W_{shield} R_{trip} > V_{active}^2 K_{scale}$$

In another embodiment, to avoid division calculation, a resistance fault is determined if the logic network evaluates the following expression as true (when $V_{active}^2$ and $I_{shield}^2$ (and/or $W_{Shield}$) are greater than their respective minimum thresholds):

$$(W_{shield} R_{trip} > V_{active}^2 K_{scale}) \text{ AND } (V_{active}^2 > V_{min}^2) \text{ AND } (I_{shield}^2 > I_{min}^2) \text{ AND } (W_{shield} > W_{min})$$

In each of the above resistance fault determinations, the following are assumed:

$V_{active}^2$=mean, squared, active electrode voltage (over a frame)
$W_{shield}$=mean, real shield power (over a frame)
$R_{trip}$=resistance below which a resistance fault is tripped.
$K_{scale}$=a scaling constant (which can be one in some configurations)
$V_{min}^2$=a constant representing the minimum level of mean, squared, active electrode voltage above which a resistance fault may trip.
$I_{shield}^2$=mean, squared shield current (over a frame)
$I_{min}^2$=a constant representing the minimum level of mean, squared, shield current above which a resistance fault may trip.
$W_{min}$=a constant representing the minimum mean, real shield power above which a resistance fault may trip.

It may also be cumbersome for an FPGA to calculate square roots in the context of RMS calculations. Instead, the pre-determined threshold can be squared.

In another embodiment, a high current fault exists if the logic circuit evaluates the following expression as true:

$$I_{shield}^2 > I_{high\_trip}^2$$

Where:

$I_{shield}^2$=mean, squared shield current (over a frame)
$I_{high\_trip}^2$=a constant representing the square of current above which a high current fault is tripped. This constant may include additional scaling.

In another embodiment, a low current fault exists if the logic circuit evaluates the following expression as true:

$$(I_{shield}^2 > I_{low\_trip}^2) \text{ AND } (V_{active}^2 < V_{max}^2)$$

Where:

$I_{shield}^2$=mean, squared shield current (over a frame)
$I_{low\_trip}^2$=a constant representing the square of current above which a low current fault is tripped. This constant may include additional scaling.
$V_{active}^2$=mean, squared, active electrode voltage (over a frame)

$V_{max}^2$ = a constant representing the maximum value of mean, squared, active electrode voltage below which a low-current fault may trip.

In another embodiment, a power fault exists if the if the logic circuit evaluates the following expression as true:

$$(W_{shield} > W_{trip})$$

In another embodiment, a power fault exists if the if the logic circuit evaluates the following expression as true:

$$(W_{shield} > W_{trip}) \text{ AND } (V_{active}^2 > V_{min}^2) \text{ AND } (I_{shield}^2 > I_{min}^2)$$

In each of the above power fault determinations, the following are assumed:

$W_{shield}$ = mean, real power in the shield (over a frame)

$W_{trip}$ = a constant representing the maximum average value of power (over a frame) above which a power fault may trip. This constant may require scaling.

$V_{active}^2$ = mean, squared, active electrode voltage (over a frame)

$V_{min}^2$ = a constant representing the minimum level of mean, squared, active electrode voltage above which a power fault may trip.

$I_{shield}^2$ = mean, squared shield current (over a frame)

$I_{min}^2$ = a constant representing the minimum level of mean, squared, shield current above which a power fault may trip.

In general the FPGA may be adapted to include monitoring and detecting some or all of low shield current fault, a high shield current fault, a shield resistance fault, a shield power fault, and a low capacitance between the active electrode and shield fault. Threshold limits for each of these different types of faults may be instrument class dependent. The FPGA or other processing element may operate on a curve that is more complex than the one shown in FIG. 6 to achieve similar purposes.

Another embodiment provides for a different-length of frame (for averaging parameters for fault calculations) for each class of instrument and/or surgical condition. One way to achieve such an embodiment is to calculate short frames for all of the parameters (e.g., 1.6 ms long) and then to average a variable number of the short frames (e.g., a long frame might be comprised of 32 short frames) based on the class of instrument and/or surgical condition. A similar fault detection technique may be implemented for both hand-switched and foot switched instruments because they generally share the same classes for fault thresholds.

Other aspects include the ability to customize threshold levels or scaling constants used in determining various types of faults based on differences in the components used to sense voltage and current from circuit board to circuit board. In the embodiment shown in FIGS. 3 and 4, these thresholds may be stored in a separate memory element 352 or 547 respectively. Electrically Erasable Programmable Read-Only Memory (EEPROM) is a type of non-volatile memory used in computers and other electronic devices to store data that must be saved when power is removed, e.g., calibration tables or device configuration. EEPROMs are useful for the type of calibration data stored in connection with various fault detection schemes that may be used in connection with aspects of the present invention. Memory element 547 may be an EEPROM or other memory device. Use of such non-volatile memory avoids the difficulty of having to adjust actual circuit components such as resistors or capacitors during factory calibration. The circuitry may alternatively be designed to recognize electrosurgical instruments that require different fault threshold levels or frame lengths because of the conditions under which they must operate. Multiple sets of fault threshold levels can be stored digitally for use with a multiplicity of instruments.

Among the parameters that may be stored in the memory element 547 is the amount of phase delay to be programmed into one or more of the high-speed ADC clocks (Active current, Active Voltage, and Shield Current) using one or more digital clock managers (DCMs) in the FPGA. This allows most of the small (but often significant) differences in phase between voltage and current for the active and shield power measurements (partly due to component variation) to be trimmed out during calibration.

Devices constructed in accordance with aspects of the present invention can detect conditions not possible using predicate systems such as a disconnected shield wire or significant power developed between the shield and the active electrode. Also, by using average, real power consumed in the shield as one of the detection mechanisms, the amount of capacitance between the active electrode and the shield does not contribute to the power consumed in the shield and does not affect the fault detection due to excessive real power consumption in the shield.

Aspects of the present invention allow the same monitor to be used with various instruments that may require different fault threshold levels or frame lengths. Thus, variations in instrument design and electrosurgical waveforms do not affect system performance or require special monitoring configurations.

An example using the general embodiment, equations, and terms described above utilizes a monopolar, foot-switched, shielded active electrode being keyed under the following conditions and with the following constants over the previous frame:

Measured Parameters:
  $V_{active}^2$ = (73 Volts, RMS)$^2$
  $I_{shield}^2$ = (0.670 Amps, RMS)$^2$
  $W_{shield}$ = 35 W Constants for this class of electrosurgical instrument:
  $V_{min}^2$ = (30 Volts, RMS)$^2$
  $I_{min}^2$ = (0.050 Amps, RMS)$^2$
  $W_{min}$ = 3 Watts
  $V_{max}^2$ = (150 Volts, RMS)$^2$
  $Z_{fault}^2$ = (10,610 ohms-magnitude)$^2$ = $1/(2\pi 500 \text{ kHz } 30 \text{ pF})^2$
  $R_{trip}$ = 2000 ohms
  $K_{scale}$ = 1
  $I_{low\_trip}$ = 0.300 Amps, RMS
  $I_{high\_trip}$ = 0.650 Amps, RMS
  $W_{trip}$ = 10 Watts Time to re-enable this class of instrument after fault: 10 seconds Under these measured parameters, with these constants, and using the equations described above, the high-current fault, power fault, and resistance faults were shown to trip contemporaneously and essentially simultaneously. The low-current fault did not trip because the active voltage was too large. The capacitance fault did not trip because the overall impedance between the active electrode and the shield was much too low. As a result of having at least one fault condition, the logic (e.g. 548) disabled the power to the coil for the active control relay (e.g. 518) which disabled the power to the active electrode (e.g. 504). In addition, the logic issued feedback to the users including audible and visible alarm indications. For this particular class of instrument, the logic (e.g. 548) re-enabled the power to the coil for the active control relay (e.g. 518) in ten seconds.

Those skilled in the art can readily recognize that numerous variations and substitutions may be made in the invention, its use and its configuration to achieve substantially the same results as achieved by the embodiments described herein. Accordingly, there is no intention to limit the invention to the disclosed exemplary forms. Many variations, modifications and alternative constructions fall within the scope and spirit of the disclosed invention.

What is claimed is:

1. A method of detecting faults within a shielded electrosurgical instrument, the shielded electrosurgical instrument having an active electrode, the method comprising:
   contemporaneously sensing an active voltage in the active electrode and a power in the electrosurgical instrument shield;
   determining whether a resistance fault exists, wherein determining whether a resistance fault exists comprises determining whether the expression $W_{shield} R_{trip} > V_{active}^2 K_{scale}$ is true, wherein $V_{active}^2$ is equal to the mean, squared, active electrode voltage over a frame, wherein $W_{shield}$ is equal to the mean, real shield power over a frame, wherein $R_{trip}$ is equal to the resistance below which a resistance fault is tripped, and wherein $K_{scale}$ is equal to a scaling constant;
   determining at least one of:
   (a) whether one or more current faults exists;
   (b) whether a power fault exists; or
   (c) whether a capacitance fault exists; and
   altering power delivery to the active electrode if any of the resistance fault, current faults, power fault, or capacitance faults exist.

2. The method of claim 1, wherein determining whether a current fault exists comprises determining whether the expression $I_{shield}^2 > I_{trip}^2$ is true, wherein $I_{shield}^2$ is equal to the mean, squared shield current over a frame, and wherein $I_{trip}^2$ is equal to a constant representing the square of current below which a current fault is tripped.

3. The method of claim 1, wherein determining whether a capacitance fault exists comprises determining whether the expression $V_{active}^2 > I_{shield}^2 Z_{fault}^2$ is true, wherein $V_{active}^2$ is equal to the mean, squared, active electrode voltage over a frame, wherein $I_{shield}^2$ is equal to the mean, squared, shield current over a frame, and wherein $Z_{fault}^2$ is equal to a constant representing the square of the magnitude of the impedance at which a capacitance fault should be tripped.

4. The method of claim 1, wherein determining whether a power fault exists comprises determining whether the expression ($W_{shield} > W_{trip}$) is true, where $W_{shield}$ is equal to the mean, real power in the shield and $W_{trip}$ is equal to a constant representing the maximum average value of power above which a power fault may trip.

5. The method of claim 1, further comprising
   detecting a shield current value; and
   determining whether a low shield current fault exists, wherein a low shield current fault exists if the following expression is true: $(I_{shield}^2 > I_{low\_trip}^2)$ AND $(V_{active}^2 < V_{max}^2)$; wherein
   $I_{shield}^2$ is a mean square of the shield current value;
   $I_{low\_trip}^2$ is a constant representing the square of current above which a low current fault is tripped;
   $V_{active}^2$ is a mean square of the active voltage in the active electrode; and
   $V_{max}^2$ is a constant representing the maximum value of mean, squared, active electrode voltage below which a low-current fault may trip.

6. A system for detecting faults within a shielded electrosurgical instrument, the electrosurgical instrument having an active electrode and a shield, the system comprising:
   a processor;
   a logic circuit;
   a memory element;
   an electrosurgical generator adapted to couple to the electrosurgical instrument and adapted to deliver power through the electrosurgical instrument; and
   monitoring circuitry coupled to the electrosurgical generator and the electrosurgical instrument, the monitoring circuitry comprising structure for contemporaneously detecting an active voltage in the active electrode and a power in the electrosurgical shield;
   the monitoring circuitry further comprising structure for determining whether a resistance fault exists, wherein determining whether a resistance fault exists comprises determining whether the expression $W_{shield} R_{trip} > V_{active}^2 K_{scale}$ is true, wherein $V_{active}^2$ is equal to the mean, squared, active electrode voltage over a frame, wherein $W_{shield}$ is equal to the mean, real shield power over a frame, wherein $R_{trip}$ is equal to the resistance below which a resistance fault is tripped, and wherein $K_{scale}$ is equal to a scaling constant, the monitoring circuitry further comprising structure for determining at least one of (a) whether one or more current faults exists, (b) whether a power fault exists, or (c) whether a capacitance fault exists;
   the monitoring circuitry further configured to generate a signal to cause the system to alter power delivery to the active electrode if any of the resistance fault, current faults, power fault, or capacitance faults exist.

7. The system of claim 6, wherein:
   determining whether a current fault exists comprises determining whether the expression $I_{shield}^2 > I_{trip}^2$ is true, wherein $I_{shield}^2$ is equal to the mean, squared shield current over a frame, and wherein $I_{trip}^2$ is equal to a constant representing the square of current below which a current fault is tripped.

8. The system of claim 6, wherein:
   determining whether a capacitance fault exists comprises determining whether the expression $V_{active}^2 > I_{shield}^2 Z_{fault}^2$ is true, wherein $V_{active}^2$ is equal to the mean, squared, active electrode voltage over a frame, wherein $I_{shield}^2$ is equal to the mean, squared, shield current over a frame, and wherein $Z_{fault}^2$ is equal to a constant representing the square of the magnitude of the impedance at which a capacitance fault should be tripped.

9. The system of claim 6, wherein:
   determining whether a power fault exists comprises determining whether the expression ($W_{shield} > W_{trip}$) is true, where $W_{shield}$ is equal to the mean, real power in the shield and $W_{trip}$ is equal to a constant representing the maximum average value of power above which a power fault may trip.

10. The system of claim 6, wherein the monitoring circuitry comprises at least one of a capacitive divider or a current transformer.

11. The system of claim 6, further comprising at least one of:
    structure for displaying at least one of (a) the power delivered to the patient and the active electrode, (b) the active electrode current, (c) the return electrode current, (d) the active electrode voltage, (e) the shield power, (f) the shield current, (g) the shield resistance, or (h) shield fault status; or
    structure for recording at least one of (a) the power delivered to the patient and the active electrode, (b) the active electrode current, (c) the return electrode current, (d) the active electrode voltage, (e) the shield power, (f) the shield current, (g) the shield resistance, or (h) shield fault status.

12. The system of claim 6, wherein the processor is adapted to determine whether a low shield current fault exists.

13. The system of claim 6, wherein
the monitoring circuitry further comprises structure for detecting a shield current value; and
the processor is adapted to determine whether a low shield current fault exists, wherein a low shield current fault exists if the following expression is true: $(I_{shield}^2 > I_{low\_trip}^2)$ AND $(V_{active}^2 < V_{max}^2)$; wherein
$I_{shield}^2$ is a mean square of the shield current value;
$I_{low\_trip}^2$ is a constant representing the square of current above which a low current fault is tripped;
$V_{active}^2$ is a mean square of the active voltage in the active electrode; and
$V_{max}^2$ is a constant representing the maximum value of mean, squared, active electrode voltage below which a low-current fault may trip.

14. The system of claim 6, wherein the electrosurgical generator and the monitoring circuitry are integrated into the same device.

15. The system of claim 6, further comprising an identification element that indicates to the monitoring circuitry a specific set of fault threshold criteria.

16. The system of claim 6, further comprising an identification element that indicates to the monitoring circuitry a class of the electrosurgical instrument.

17. A method of detecting faults within a shielded electrosurgical instrument, the shielded electrosurgical instrument having an active electrode, the method comprising:
contemporaneously sensing an active voltage in the active electrode and a power in the electrosurgical instrument shield;
determining at least two of: (a) whether a resistance fault exists, (b) whether one or more current faults exists, (c) whether a power fault exists, or (d) whether a capacitance fault exists; and
altering power delivery to the active electrode if any of the resistance fault, current faults, power fault, or capacitance faults exist; wherein
determining whether a resistance fault exists comprises determining whether the expression $W_{shield} R_{trip} > V_{active}^2 K_{scale}$ is true, wherein $V_{active}^2$ is equal to the mean, squared, active electrode voltage over a frame, wherein $W_{shield}$ is equal to the mean, real shield power over a frame, wherein $R_{trip}$ is equal to the resistance below which a resistance fault is tripped, and wherein $K_{scale}$ is equal to a scaling constant;
determining whether a current fault exists comprises determining whether the expression $I_{shield}^2 > I_{trip}^2$ is true, wherein $I_{shield}$ is equal to the mean, squared shield current over a frame, and wherein $I_{trip}^2$ is equal to a constant representing the square of current below which a current fault is tripped;
determining whether a capacitance fault exists comprises determining whether the expression $V_{active}^2 > Z_{fault}^2$ is true, wherein $V_{active}^2$ is equal to the mean, squared, active electrode voltage over a frame, wherein $I_{shield}^2$ is equal to the mean, squared, shield current over a frame, and wherein $Z_{fault}^2$ is equal to a constant representing the square of the magnitude of the impedance at which a capacitance fault should be tripped; and wherein
determining whether a power fault exists comprises determining whether the expression $(W_{shield} > W_{trip})$ is true, where $W_{shield}$ is equal to the mean, real power in the shield and $W_{trip}$ is equal to a constant representing the maximum average value of power above which a power fault may trip.

18. The method of claim 17, further comprising
detecting a shield current value; and
determining whether a low shield current fault exists, wherein determining whether a low shield current fault exists comprises determining whether the expressions $(I_{shield}^2 > I_{low\_trip}^2)$ AND $(V_{active}^2 < V_{max}^2)$ are true; wherein
$I_{shield}^2$ is a mean square of the shield current value;
$I_{low\_trip}^2$ is a constant representing the square of current above which a low current fault is tripped;
$V_{active}^2$ is a mean square of the active voltage in the active electrode; and
$V_{max}^2$ is a constant representing the maximum value of mean, squared, active electrode voltage below which a low-current fault may trip.

19. A method of detecting faults within a shielded electrosurgical instrument, the shielded electrosurgical instrument having an active electrode, the method comprising:
contemporaneously sensing an active voltage in the active electrode and a power in the electrosurgical instrument shield;
determining
whether one or more current faults exists, wherein determining whether one or more current faults exist comprises determining whether the expression $I_{shield}^2 > I_{trip}^2$ is true, wherein $I_{shield}^2$ is equal to the mean, squared shield current over a frame, and wherein $I_{trip}^2$ is equal to a constant representing the square of current below which a current fault is tripped;
determining at least one of: (a) whether a resistance fault exists, (b) whether a power fault exists, or (c) whether a capacitance fault exists; and
altering power delivery to the active electrode if any of the resistance fault, current faults, power fault, or capacitance faults exist.

20. A method of detecting faults within a shielded electrosurgical instrument, the shielded electrosurgical instrument having an active electrode, the method comprising:
contemporaneously sensing an active voltage in the active electrode and a power in the electrosurgical instrument shield;
determining at least one of:
whether a resistance fault exists;
whether one or more current faults exists; or
whether a power fault exists;
determining whether a capacitance fault exists, wherein determining whether a capacitance fault exists comprises determining whether the expression $V_{active}^2 > I_{shield}^2 Z_{fault}^2$ is true, wherein $V_{active}^2$ is equal to the mean, squared, active electrode voltage over a frame, wherein $I_{shield}^2$ is equal to the mean, squared, shield current over a frame, and wherein $Z_{fault}^2$ is equal to a constant representing the square of the magnitude of the impedance at which a capacitance fault should be tripped; and
altering power delivery to the active electrode if any of the resistance fault, current faults, power fault, or capacitance faults exist.

21. A system for detecting faults within a shielded electro surgical instrument, the electrosurgical instrument having an active electrode and a shield, the system comprising:
a processor;

a logic circuit;
a memory element;
an electrosurgical generator adapted to couple to the electrosurgical instrument and adapted to deliver power through the electrosurgical instrument; and
monitoring circuitry coupled to the electro surgical generator and the electro surgical instrument, the monitoring circuitry comprising structure for contemporaneously detecting an active voltage in the active electrode and a power in the electrosurgical shield;
the monitoring circuitry further comprising structure for determining at least one of (a) whether a resistance fault exists, (b) whether a power fault exists, or (c) whether a capacitance fault exists,
the monitoring circuitry further comprising structure for determining whether one or more current faults exists, wherein determining whether one or more current faults exist comprises determining whether the expression $I_{shield}^2 > I_{trip}^2$ is true, wherein $I_{shield}^2$ is equal to the mean, squared shield current over a frame, and wherein $I_{trip}^2$ is equal to a constant representing the square of current below which a current fault is tripped;
the monitoring circuitry further configured to generate a signal to cause the system to alter power delivery to the active electrode if any of the resistance fault, current faults, power fault, or capacitance faults exist.

22. A system for detecting faults within a shielded electro surgical instrument, the electrosurgical instrument having an active electrode and a shield, the system comprising:
a processor;
a logic circuit;
a memory element;
an electrosurgical generator adapted to couple to the electrosurgical instrument and adapted to deliver power through the electrosurgical instrument; and
monitoring circuitry coupled to the electro surgical generator and the electro surgical instrument, the monitoring circuitry comprising structure for contemporaneously detecting an active voltage in the active electrode and a power in the electrosurgical shield;
the monitoring circuitry further comprising structure for determining at least one of (a) whether a resistance fault exists, (b) whether one or more current faults exists, or (c) whether a power fault exists;
the monitoring circuitry further comprising structure for determining whether a capacitance fault exists, wherein determining whether a capacitance fault exists comprises determining whether the expression $V_{active}^2 > I_{shield}^2 Z_{fault}^2$ is true, wherein $V_{active}^2$ is equal to the mean, squared, active electrode voltage over a frame, wherein $I_{shield}^2$ is equal to the mean, squared, shield current over a frame, and wherein $Z_{fault}^2$ is equal to a constant representing the square of the magnitude of the impedance at which a capacitance fault should be tripped;
the monitoring circuitry further configured to generate a signal to cause the system to alter power delivery to the active electrode if any of the resistance fault, current faults, power fault, or capacitance faults exist.

* * * * *